United States Patent
Koh et al.

(10) Patent No.: US 9,828,395 B2
(45) Date of Patent: Nov. 28, 2017

(54) NANOCRYSTAL AND PREPARATION METHOD THEREOF

(71) Applicant: SAMSUNG ELECTRONICS CO., LTD., Suwon-si (KR)

(72) Inventors: Weonkyu Koh, Suwon-si (KR); Sungjun Park, Hwaseong-si (KR); Dongjin Yun, Pohang-si (KR); Junho Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/255,369

(22) Filed: Sep. 2, 2016

(65) Prior Publication Data

US 2017/0260218 A1     Sep. 14, 2017

(30) Foreign Application Priority Data

Mar. 10, 2016    (KR) .................... 10-2016-0029099

(51) Int. Cl.
| | |
|---|---|
| *H01L 51/00* | (2006.01) |
| *C07F 9/38* | (2006.01) |
| *C09K 11/06* | (2006.01) |
| *B82Y 40/00* | (2011.01) |
| *B82Y 20/00* | (2011.01) |
| *H01L 51/50* | (2006.01) |

(52) U.S. Cl.
CPC ............ *C07F 9/3808* (2013.01); *C09K 11/06* (2013.01); *H01L 51/005* (2013.01); *B82Y 20/00* (2013.01); *B82Y 40/00* (2013.01); *C09K 2211/181* (2013.01); *H01L 51/502* (2013.01); *Y10S 977/774* (2013.01); *Y10S 977/896* (2013.01); *Y10S 977/95* (2013.01)

(58) Field of Classification Search
USPC .............................................. 556/19, 81, 83
See application file for complete search history.

(56) References Cited

U.S. PATENT DOCUMENTS

| | | |
|---|---|---|
| 2003/0170918 A1 | 9/2003 | Dehaven et al. |
| 2006/0234480 A1 | 10/2006 | Dehaven et al. |
| 2006/0270100 A1 | 11/2006 | DeHaven et al. |
| 2012/0126216 A1 | 5/2012 | Dehaven et al. |
| 2013/0320836 A1 | 12/2013 | Kanatzidis et al. |

FOREIGN PATENT DOCUMENTS

| | | |
|---|---|---|
| CN | 101687385 A | 3/2010 |
| CN | 104388089 A | 3/2015 |
| WO | 2013126385 A1 | 8/2013 |

OTHER PUBLICATIONS

Sun, ACS Nano, 2016, 10, 3648-3657; Published online Feb. 17, 2016.*
Park et al: "Room Temperature Single-Photon Emission from Individual Perovskite Quantum Dots" ACS Nano, Aug. 27, 2015, American Chemical Society, pp. 1-22, (23 pages total).
Protesescu et al: "Nanocrystals of Cesium Lead Halide Perovskites (CsPbX3, X = Cl, Br, and I): Novel Optoelectronic Materials Showing Bright Emission with Wide Color Gamut" ACS Publications, American Chemical Society, Feb. 2, 2015, pp. 3692-3696 (5 pages total).
Niu et al: "Review of recent progress in chemical stability of perovskite solar cells" Journal of Materials Chemistry A, 2015, 3, pp. 8970-8980, The Royal Society of Chemistry (11 pages total).
Stranks et al: "Metal-halide perovskites for photovoltaic and light-emitting devices" Nature Nanotechnology, vol. 10, May 7, 2015, Macmillan Publishers Limited., pp. 391-402 (12 pages total).
Woo et al: "Air-Stable PbSe Nanocrystals Passivated by Phosphonic Acids", Dec. 29, 2015, Journal of the American Chemical Society, pp. 1-9 (10 pages total).
Mokari et al: "Shape, Size, and Assembly Control of PbTe Nanocrystals" J. Am. Chem. Soc., Jun. 7, 2007, American Chemical Society, vol. 129, No. 32, pp. 9864-9865, (2 pages total).
Jeon et al: "Compositional engineering of perovskite materials for high-performance solar cells", Nature, vol. 517, Jan. 22, 2015, Macmillan Publishers Limited, (14 pages total).
Yang et al: "High-performance photovoltaic perovskite layers fabricated through intramolecular exchange" vol. 348, Issue 6240, Jun. 12, 2015, pp. 1234-1237 (5 pages total).
Anonymous: "Solar cell efficiency" Wikipedia, the free encyclopedia, https://en.wlklpedla.org/wlkl/Solar_cell_efficiency, pp. 1-7 (7 pages total) (last modified Aug. 12, 2016).

\* cited by examiner

*Primary Examiner* — Pancham Bakshi
(74) *Attorney, Agent, or Firm* — Sughrue Mion, PLLC

(57) ABSTRACT

A nanocrystal represented by the following Formula 1 and a preparation method thereof:

$$AMX_3L \qquad \text{Formula 1}$$

wherein A is cesium (Cs), rubidium (Rb), or an ammonium salt,
M is germanium (Ge), tin (Sn), or lead (Pb),
X is one or more selected from Cl, Br and I, and
L is an organic functional group having one terminal selected from a phosphonic acid group, a carboxylic acid group, and an amino group.

19 Claims, 10 Drawing Sheets

NANOCRYSTAL AND PREPARATION METHOD THEREOF

CROSS-REFERENCE TO RELATED APPLICATION

This application claims benefit to Korean Patent Application No. 10-2016-0029099, filed on Mar. 10, 2016, in the Korean Intellectual Property Office, the disclosure of which is incorporated herein by reference in its entirety.

BACKGROUND

1. Field

The present disclosure relates to a nanocrystal and a preparation method thereof.

2. Description of the Related Art

In colloidal perovskite quantum dots, iodine containing compounds show reduced thermal and chemical stability when they are used in photoelectronic devices, which is an obstacle to their practical application.

In order to solve this problem, the use of a chemical composition such as formamidinium or the like, together with an ammonium salt has been proposed for bulk perovskite. However, when this method was applied to colloidal nanocrystals, thermal and chemical stability did not reach a satisfactory level. Accordingly, improvement thereof is required.

SUMMARY

An aspect of the present disclosure provides a nanocrystal with improved stability.

Another aspect provides a preparation method for the above-described nanocrystal.

According to an aspect of the present disclosure, provided herein is a nanocrystal represented by the following Formula 1:

  [Formula 1]

In Formula 1, A is cesium (Cs), rubidium (Rb), or an ammonium salt, M is germanium (Ge), tin (Sn), or lead (Pb), X is one or more selected from Cl, Br and I, and L is an organic functional group having one terminal selected from a phosphonic acid group, a carboxylic acid group, and an amino group.

According to another aspect of the present disclosure, there is provided a method of preparing the nanocrystal, the method including the steps of mixing a metal halide containing one or more selected from germanium (Ge), tin (Sn), and lead (Pb) with a solvent, and drying the mixture; and a step of adding, to the dried mixture, a surfactant, a compound containing an organic functional group having one terminal selected from a phosphonic acid group, a carboxylic acid group, and an amino group, and an organic acid containing one or more selected from cesium (Cs), rubidium (Rb), and an ammonium salt; followed by a step of mixing and heat-treatment to prepare the above-described nanocrystal.

BRIEF DESCRIPTION OF THE DRAWINGS

These and/or other aspects will become apparent and more readily appreciated from the following description of embodiments of the present disclosure, taken in conjunction with the accompanying drawings in which.

DETAILED DESCRIPTION

A nanocrystal, a preparation method thereof, and a photoelectronic device using the nanocrystal will be described below in more detail with reference to the accompanying drawings.

Provided is a nanocrystal represented by the following Formula 1:

  [Formula 1], wherein A is Cs, Rb, or an ammonium salt,

M is Ge, Sn, or Pb,

X is one or more selected from Cl, Br and I, and

L is an organic functional group having one terminal selected from a phosphonic acid group, a carboxylic acid group, and an amino group.

The organic functional group having one terminal selected from a phosphonic acid group, a carboxylic acid group, and an amino group has 4 to 20 carbon atoms, and in preferable embodiments contains 8 to 20 carbon atoms.

As used herein, the term "nanocrystal" means that the particle size or particle diameter is several hundred nanometers. The nanocrystal may have a diameter of, for example, about 100 nm or less, and for example, may have a diameter that ranges from about 1 nm to about 100 nm.

The ammonium salt is represented by the formula $-N(R)_4^+$, wherein each R is the same as or different from each other, and represents hydrogen, a $C_1$-$C_{10}$ alkyl group, or a $C_6$-$C_{20}$ aryl group. The ammonium salt may be exemplified by $-N(CH_2CH_3)_4^+$ or $-N(CH_3)_4^+$.

The amino group is represented by the formula $-N(R_1)(R_2)$, wherein $R_1$ and $R_2$ are each independently hydrogen, a $C_1$ to $C_{10}$ alkyl group, or a $C_6$ to $C_{20}$ aryl group.

The organic functional group having one terminal selected from a phosphonic acid group, a carboxylic acid group, and an amino group is represented by the formulae $L_1$-P(=O)(OH)$_2$, $L_1$-C(=O)(OH), or $L_1$-N(R$_1$)(R$_2$), wherein $L_1$ is a chemical bond, a $C_4$ to $C_{20}$ alkyl group, a $C_6$ to $C_{20}$ aryl group, or a $C_4$ to $C_{20}$ heteroaryl group; and $R_1$ and $R_2$ are each independently hydrogen, a $C_1$ to $C_{10}$ alkyl group, or a $C_6$ to $C_{20}$ aryl group. When $L_1$ is a $C_4$ to $C_{20}$ alkyl group, a $C_6$ to $C_{20}$ aryl group, or a $C_4$ to $C_{20}$ heteroaryl group, $L_1$ is a hydrophobic ligand, and thus the nanocrystal has very excellent stability.

Figure 1:
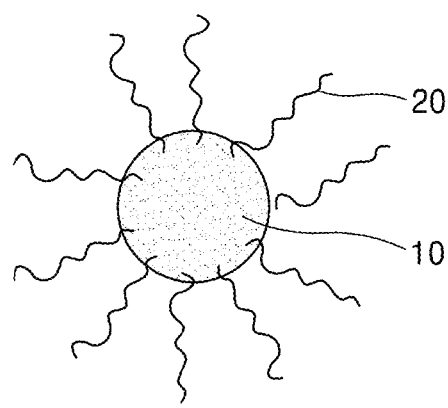
FIG. 1 shows a structure of a nanocrystal according to an embodiment.

FIG. 1 shows a schematic illustration of a nanocrystal according to an embodiment of the present disclosure.

Referring to this illustration, the nanocrystal is a metal-ligand complex having a structure, in which a core 10 includes $AMX_3$ (wherein A, M and X are the same as defined in Formula 1) and ligands (L) 20 bind to the surface of the core 10. The ligand is a $C_4$ to $C_{20}$ organic functional group containing a phosphonic acid group, a carboxylic acid group, or an amino group. Owing to this ligand, the stability of the nanocrystal is greatly improved. When X in $AMX_3$ constituting the core 10 is iodine, thermal and chemical stability is rapidly decreased, but the nanocrystal according to an embodiment of the present disclosure has improved stability because the nanocrystal includes the ligand (L) as represented by Formula 1. Therefore, the nanocrystal may be used to easily prepare colloidal quantum dots.

The $C_4$ to $C_{20}$ organic functional group containing a phosphonic acid group, a carboxylic acid group, or an amino group is, for example, $-CH_3(CH_2)_{12}P(=O)(OH)_2$. As the ligand, the organic functional group containing a phosphonic acid group, a carboxylic acid group, or an amino group binds to the core 10 via a $P(=O)-O$ moiety, an N moiety, or a $C(=O)-O$ moiety, which exhibit a strong bond between the core and the ligand. The nanocrystal has improved dispersity in a non-polar solvent as a result of a hydrophobic alkyl group present in the ligand (e.g., $CH_3(CH_2)_{12}-$).

The following Reaction Scheme 1 represents a nanocrystal using an organic functional group containing a phosphonic acid group as a ligand.

Reaction Scheme 1:

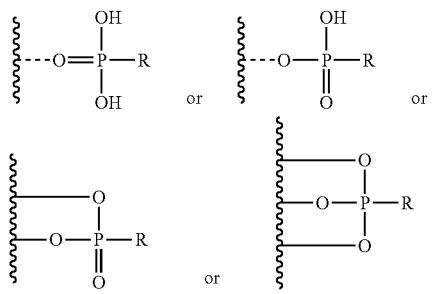

In Reaction Scheme 1, $RP(=O)(OH)_2$ represents the ligand, and the ligand binds to the core to form a variety of types. In Reaction Scheme 1, R represents $L_1$ of a ligand $L_1\text{-}P(=O)(OH)_2$.

The ligand maintains a strong surface ligand bond without interfering with the crystal growth of the core. As a result, the stability of the quantum dots is greatly increased.

The nanocrystal, for example, represented by Formula 1 may be a compound represented by the following Formula 2:

$$AMI_xBr_{3-x}L \qquad \text{Formula 2}$$

wherein A is cesium (Cs), rubidium (Rb), or an ammonium salt,

M is Ge, Sn, or Pb, x satisfies the relationship $0 < x \leq 3$, and

L is a $C_4$ to $C_{20}$ organic functional group having one terminal selected from a phosphonic acid group, a carboxylic acid group, and an amino group.

The nanocrystal may be a compound represented by the following Formula 3:

$$CsPbI_xBr_{3-x}L \qquad \text{Formula 3}$$

wherein x satisfies the relationship $0 < x \leq 3$,

L is $L_1\text{-}P(=O)(OH)_2$, $-L_1\text{-}C(=O)(OH)$, or $-L_1-N(R_1)(R_2)$, wherein $L_1$ is a chemical bond, a $C_4$ to $C_{20}$ alkyl group, a $C_6$ to $C_{20}$ aryl group, or a $C_4$ to $C_{20}$ heteroaryl group; and $R_1$ and $R_2$ are each independently hydrogen, a $C_1$ to $C_{10}$ alkyl group, or a $C_6$ to $C_{20}$ aryl group.

The nanocrystal may be a compound represented by the following Formula 4:

$$CsPbI_xBr_{3-x}L \qquad \text{Formula 4}$$

wherein L is $CH_3(CH_2)_6P(=O)(OH)_2$, $CH_3(CH_2)_7P(=O)(OH)_2$, $CH_3(CH_2)_8P(=O)(OH)_2$, $CH_3(CH_2)_9P(=O)(OH)_2$, $CH_3(CH_2)_{10}P(=O)(OH)_2$, $CH_3(CH_2)_{11}P(=O)(OH)_2$, or $CH_3(CH_2)_{12}P(=O)(OH)_2$, and x satisfies the relationship $0 < x \leq 3$.

The nanocrystal according to an embodiment of the present disclosure, for example, $AMX_3$ of Formula 1 or $CsPbI_xBr_{3-x}$ of Formula 4, is $CsPbI_3$, $CsPbBr_{1.92}I_{1.08}$, $CsPbBr_{1.8}I_{1.2}$, $CsPbBr_{1.7}I_{1.3}$, $CsPbBr_{1.6}I_{1.4}$, $CsPbBr_{1.1}I_{1.9}B$, $CsPbBr_{1.2}I_{1.8}B$, $CsPbBr_{0.9}I_{2.1}$, $CsPbBr_{0.7}I_{2.3}$, $CsPbBr_{0.5}I_{2.5}$, $CsPbBr_{0.3}I_{2.7}$, $CsPbBr_{0.1}I_{2.9}$, wherein L is $CH_3(CH_2)_6P(=O)(OH)_2$, $CH_3(CH_2)_7P(=O)(OH)_2$, $CH_3(CH_2)_8P(=O)(OH)_2$, $CH_3(CH_2)_9P(=O)(OH)_2$, $CH_3(CH_2)_{10}P(=O)(OH)_2$, $CH_3(CH_2)_{11}P(=O)(OH)_2$, or $CH_3(CH_2)_{12}P(=O)(OH)_2$.

The nanocrystal represented by Formula 1 may be, for example, a nanocrystal of $CsPbBr_{1.92}I_{1.08}L$, wherein L is $CH_3(CH_2)_{12}P(=O)(OH)_2$, $CH_3(CH_2)_{11}P(=O)(OH)_2$, or $CH_3(CH_2)_{10}P(=O)(OH)_2$; or a nanocrystal of $CsPbI_3L$, wherein L is $CH_3(CH_2)_{12}P(=O)(OH)_2$, $CH_3(CH_2)_{11}P(=O)(OH)_2$, or $CH_3(CH_2)_{10}P(=O)(OH)_2$.

The emission wavelength of the nanocrystal is from about 500 nm to about 700 nm, and the difference in the emission wavelength after 1 week is less than about 50 nm, and for example may be from about 1 nm to about 40 nm. Herein, the difference in the emission wavelength represents the difference between the emission wavelength of the nanocrystal after 1 week and the initial emission wavelength of the nanocrystal.

The content of the one or more atoms selected from Cl, Br and I, which are extracted from the nanocrystal into an aqueous layer, is about 80 mg/l or less, and the content of the one or more atoms selected from cesium (Cs) and rubidium (Rb), which are extracted from the nanocrystal into an aqueous layer, is about 40 mg/l or less. Such a reduction in the content of each ion extracted from the nanocrystal means great improvement of stability.

The nanocrystal in one embodiment herein is a colloidal perovskite quantum dot. It is possible to use the quantum dot in core-shell, alloy, doping structures, and the like. This quantum dot may be used as a material in a light emitting device, and usefully applied to color tuning.

The quantum dot is useful in the fields of a perovskite solar cell, a light receiving device, an LED, a laser, and the like, and exhibits an efficiency of 20% or higher by a solution process. In a solution process, a precursor solution is applied to a substrate by spin coating, and then the resulting structure is dried to form a solid thin film. A solution process is achieved at lower temperature compared with vapor deposition or PVD/CVD. Thus, a solution process is useful in the fields of flexible/stretchable devices. A method of measuring efficiency is disclosed in, e.g., https://en.wikipedia.org/wiki/Solar_cell_efficiency; *Nature* 517, 476 (2015); and *Science* 348, 1234 (2015).

A structure of the nanocrystal according to an embodiment of the present disclosure may be confirmed by X-ray photoelectron spectroscopy (XPS), energy-dispersive X-ray spectroscopy (EDAX), inductively coupled plasma spectroscopy (ICP) and/or mass spectrometry.

A method of preparing the nanocrystal according to an embodiment is described below.

A metal halide containing one or more atoms selected from Ge, Sn and Pb is mixed with a solvent, and a process of drying the mixture is performed.

The drying process is, for example, performed under vacuum at a temperature of 80 to 150° C.

The solvent may be, for example, one or more selected from 1-octadecene, 1-decene, 1-undecene, 1-dodecene, 1-tetradecene, 1-hexadecene, and 1-eicosene. The content of the solvent may be from about 100 parts by weight to about 3000 parts by weight, based on 100 total parts by weight of the organic acid containing one or more selected from cesium (Cs), rubidium (Rb), and ammonium salt and the metal halide.

The organic acid containing one or more items selected from cesium (Cs), rubidium (Rb), and ammonium salt may be cesium oleate, rubidium oleate, or the like. The metal halide may be one or more selected from lead iodide ($PbI_2$), lead bromide ($PbBr_2$), germanium iodide ($GeI_2$), germanium bromide ($GeBr_2$), tin iodide ($SnI_2$), and tin bromide ($SnBr_2$).

To the dried mixture, a surfactant, a compound containing an organic functional group having one terminal selected from a phosphonic acid group, a carboxylic acid group, and an amino group, and an organic acid containing one or more selected from cesium (Cs), rubidium (Rb), and an ammonium salt may be added, followed by mixing and heat treatment thereof.

The heat treatment is performed at a temperature of from about 100° C. to about 200° C., for example at a temperature of about 120° C. to about 150° C.

The product obtained by performing the heat treatment is cooled to room temperature (about 25° C.), and then purification is performed using a method such as centrifugation or the like so as to obtain a desired product.

The surfactant may be any compound generally used, and examples include at least one selected from $C_1$-$C_{18}$ carboxylic acid, $C_1$-$C_{18}$ alkyl amine, and $C_1$-$C_{18}$ alcohol.

The $C_1$-$C_{18}$ carboxylic acid is preferably selected from oleic acid, octanoic acid, stearic acid, and decanoic acid, and the $C_1$-$C_{18}$ alkylamine is preferably at least one selected from oleylamine, octylamine, hexadecylamine, octadecylamine, and tri-n-octylamine.

The $C_1$-$C_{18}$ alcohol may be at least one selected from oleyl alcohol, octanol, and butanol.

According to one embodiment, the surfactant is one or more selected from oleylamine and oleic acid. With regard to the content of the surfactant, the surfactant is used at a conventional level.

The compound containing an organic functional group having one terminal selected from a phosphonic acid group, a carboxylic acid group, and an amino group may be 1-tetradecyl phosphonic acid, n-hexyl phosphonic acid, n-octadecyl phosphonic acid or the like.

The content of the compound containing a $C_4$ to $C_{20}$ organic functional group having one terminal selected from the phosphonic acid group, carboxylic acid group, and amino group is from about 0.1 mole to about 1 mole, for example, about 0.5 mole to about 1 mole, based on 1 mole of metal halide ($MX_3$). When the content of the compound containing an organic functional group having one terminal selected from the phosphonic acid group, carboxylic acid group, and amino group is within the above range, processability using the compound such as spin coating and the like, becomes excellent due to proper solubility and the like.

According to the preparation method, one or more items selected from the phosphonic acid group, carboxylic acid group, and amino group in the compound containing the organic functional group having one terminal selected from the phosphonic acid group, carboxylic acid group, and amino group react with the core material of the nanocrystal, for example, $CsPbI_3$, to form a metal ($CsPbI_3$)-ligand complex.

The nanocrystal according to one embodiment may be used in an photoelectronic device.

The photoelectronic device includes a device converting electrical energy into optical energy and a device converting optical energy into electrical energy using semiconductor's photoelectronic properties. The device converting electrical energy into optical energy includes a luminous device or a light emitting device such as a light emitting diode (LED) and a laser diode (LD). The device converting optical energy into electrical energy includes a solar cell, a photodiode, and the like.

Figure 7:
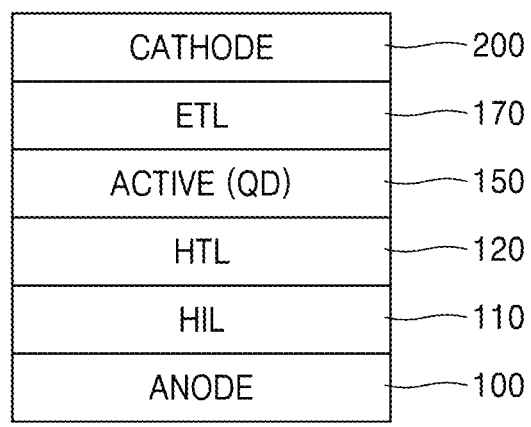
FIG. 7 is a cross-sectional view of a photoelectronic device including the nanocrystal according to an embodiment.

FIG. 7 is a cross-sectional view of a photoelectronic device including the nanocrystal according to an embodiment as a quantum dot.

Referring to FIG. 7, an anode 100 and a cathode 200 spaced therefrom may be provided. The anode 100 and the cathode 200 may be also called a first electrode and a second electrode, respectively. The anode 100 may include, for example, a transparent electrode material such as indium tin oxide (ITO) or other materials, such as Al, Ag, Au, carbon nanotube (CNT), graphene, and the like. The cathode 200 may include, for example, Al, Mo, Ag, Au, Ca, Ba, ITO, CNT, graphene, and the like. However, these mentioned materials for the anode 100 and the cathode 200 are exemplary, and other various metals, conductive compounds (oxide), and the like may be used.

An active layer 150 may be provided between the anode 100 and the cathode 200. The active layer 150 may include quantum dots.

The quantum dots of the active layer 150 may be formed, for example, using a colloidal solution. As the quantum dots, the nanocrystal according to an embodiment is used. The quantum dots may be colloidal quantum dots.

An electron transport layer (ETL) 170 may be provided between the active layer 150 and the cathode 200. The ETL 170 may include an inorganic semiconductor. The inorganic semiconductor may be an n-type semiconductor. The inorganic semiconductor may include an oxide or non-oxide. Herein, the oxide may include, for example, one of a Zn oxide ($ZnO_x$)($0<x\leq2$), a Ti oxide ($TiO_x$)($0<x\leq2$), a Sn oxide ($SnO_x$)($0<x\leq2$), and a Zr oxide ($ZrO_x$)($0<x\leq2$), or a combination of at least two thereof. The Zn oxide may be ZnO, the Ti oxide may be $TiO_2$, the Sn oxide may be $SnO_2$, and the Zr oxide may be $ZrO_2$. The non-oxide may include, for example, n-GaN. The above-mentioned specific materials for the inorganic semiconductor are exemplary, and other various inorganic semiconductor materials may be used. The ETL 170 including the inorganic semiconductor is advantageous over an electron transport layer including an organic semiconductor because a high-efficiency photoelectronic device may be obtained. However, in the following Examples, the material for the ETL 170 is not limited to an inorganic semiconductor. In some cases, the ETL 170 may include an n-type organic semiconductor.

The ETL 170 may be a general thin film type or may have a layered structure including a plurality of nanostructures. The plurality of nanostructures may be, for example, nanoparticles. The ETL 170 may be in an amorphous or polycrystalline phase, and in some cases, may be an amorphous/polycrystalline-mixed phase. When the ETL 170 includes the inorganic semiconductor, the ETL 170 may have a relatively large amount of dangling bonds on its surface. In this regard, the ETL 170 may have a relatively high surface charge density.

The photoelectronic device according to an embodiment herein may include the above-described quantum dot so as to have excellent performance and a high photoelectric conversion efficiency, and the photoelectronic device (quantum dot-applied quantum dot) may have improved durability and stability.

A hole transport layer (HTL) 120 may be further provided between the active layer 150 and the anode 100. In FIG. 7, the hole transport layer is illustrated as an essential layer, but it may be omitted.

The HTL 120 may include an organic semiconductor. The organic semiconductor may be a p-type semiconductor. The organic semiconductor may include a low molecular weight- or high molecular weight-based organic material.

Specifically, the organic semiconductor may include at least any one of poly(9,9-dioctylfluorene-co-N-(4-butylphenyl)diphenylamine) (TFB), 4,4'-bis(carbazol-9-yl)biphenyl (CBP), N,N'-bis(3-methylphenyl)-N,N'-diphenylbenzidine (TPD or poly-TPD), poly(N-vinylcarbazole) (PVK), tris(4-carbazoyl-9-ylphenyl)amine (TCTA), N,N'-diphenyl-N,N'-bis(1-naphthyl)-1,1'-biphenyl-4,4'-diamine (NPD), poly(9,9-dioctylfluorene-co-bis-N,N-phenyl-1,4-phenylenediamine (PFB), and poly(9,9-dioctylfluorene-co-bithiophene) (F8T2).

However, the above-mentioned specific materials for the HTL 120 are exemplary, and other various materials may be used as the material for the HTL 120. In some cases, the HTL 120 may include an inorganic semiconductor (p-type inorganic semiconductor).

When the HTL 120 includes an organic semiconductor, the HTL 120 may directly contact the active layer 150. Although the HTL 120 directly contacts the active layer 150, a relatively excellent interface property therebetween may be secured, and a high-efficiency photoelectronic device may be obtained. However, as mentioned above, the HTL 120 may include an inorganic semiconductor. In this case, a predetermined molecular layer (second molecular interface layer) (not shown) may be further provided between the HTL 120 and the active layer 150. Even if the HTL 120 includes an organic semiconductor, a predetermined molecular layer (second molecular interface layer) (not shown) may be further provided between the HTL 120 and the active layer 150, if necessary.

A hole injection layer (HIL) 110 may be further provided between the HTL 120 and the anode 100. The HIL 110 may include an organic semiconductor or an inorganic semiconductor. For example, the HIL 110 may include an organic semiconductor such as poly(3,4-ethylenedioxythiophene) (PEDOT) or poly(3,4-ethylenedioxythiophene):polystyrene sulfonate (PEDOT:PSS).

Further, the HIL 110 may include an inorganic semiconductor such as $MoO_3$, $NiO$, or $WO_3$. However, these specifically mentioned materials for HIL 110 are exemplary, and other various materials may be used as the material for the HIL 110. A hole injection material generally used in photoelectronic device fields may be used as the material for the HIL 110. If the HIL 110 has high conductivity, the HIL 110 may be regarded as being a part of the anode 100. In some cases, no HIL 110 may be provided. In such a case, the HTL 120 may also function as the HIL 110.

A nanocrystal according to an embodiment herein has excellent stability, and its stability in colloidal perovskite quantum dots is improved. This nanocrystal may be used to manufacture a photoelectronic device having improved performance.

Reference will now be made in detail to specific embodiments, examples of which are illustrated in the accompanying drawings, wherein like reference numerals refer to like elements throughout. In this regard, the present embodiments may have different forms and should not be construed as being limited to the descriptions set forth herein. Accordingly, embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

Hereinafter, embodiments of the present disclosure will be described in more detail with reference to the following Examples. However, the disclosure is not intended to be limited by the following Examples.

Example 1

5 ml of 1-octadecene and 0.067 g of lead iodide ($PbI_2$) were mixed, and dried under vacuum at about 100° C. for 1 hour. Then, the mixture was mixed with 0.5 ml of oleic acid, 0.5 ml of oleylamine, and 40 mg of tetradecylphosphonic acid under a nitrogen atmosphere at 120° C. to prepare a mixture. The content of tetradecylphosphonic acid was about 1 mole, based on 1 mole of lead iodide. The content of tetradecylphosphonic acid was measured by measuring the weights of tetradecylphosphonic acid and lead iodide ($PbI_2$) using an electronic scale. Then the relative content of tetradecylphosphonic acid and lead iodide ($PbI_2$) was calculated by their respective molecular weights.

When the mixture became homogenous, the reaction temperature was increased to about 150° C., and 0.5 ml of a 0.125 M cesium oleate solution in 1-octadecene was rapidly added thereto. The reaction mixture was cooled to room temperature (25° C.), and purified by centrifugation to obtain a nanocrystal $CsPbI_3L(L=CH_3(CH_2)_{12}P(=O)(OH)_2)$. This nanocrystal had a structure in which a $P(=O)(OH)_2$ moiety of a ligand $CH_3(CH_2)_{12}P(=O)(OH)_2$ bound to a core $CsPbI_3$.

Example 2

A nanocrystal was obtained in the same manner as in Example 1, except that the content of tetradecylphosphonic acid was about 0.5 mole, based on 1 mole of lead iodide, during the preparation of the mixture.

Example 3

A nanocrystal was obtained in the same manner as in Example 1, except that the content of tetradecylphosphonic acid was about 0.2 mole, based on 1 mole of lead iodide, during the preparation of the mixture.

Example 4

A nanocrystal was obtained in the same manner as in Example 1, except that the content of tetradecylphosphonic acid was about 0.1 mole, based on 1 mole of lead iodide, during the preparation of the mixture.

Example 5

5 ml of 1-octadecene, 0.067 g (0.0145 mol) of lead iodide ($PbI_2$), and 0.03 g (0.008174 mol) of lead bromide ($PbBr_2$)

were mixed, and dried under vacuum at about 100° C. for 1 hour. Then, the mixture was mixed with 0.5 ml of oleic acid, 0.5 ml of oleylamine, and 40 mg of tetradecylphosphonic acid under a nitrogen atmosphere at 120° C. to prepare a mixture. The content of tetradecylphosphonic acid was about 1 mole, based on 1 mole of lead iodide.

When the mixture became homogenous, the reaction temperature was increased to about 150° C., and 0.5 ml of a 0.125 M cesium oleate solution in 1-octadecene was rapidly added thereto. The reaction mixture was cooled to room temperature (25° C.), and purified by centrifugation to obtain a nanocrystal $CsPbBr_{1.92}I_{1.08}L$, wherein L is $CH_3(CH_2)_{12}P(=O)(OH)_2$.

Comparative Example 1

A nanocrystal $CsPbI_3$ was obtained in the same manner as in Example 1, except that no tetradecylphosphonic acid was added.

Comparative Example 2

A nanocrystal $CsPbBr_3$ was obtained in the same manner as in Example 1, except that lead bromide was used instead of lead iodide ($PbI_2$) and no tetradecylphosphonic acid was added during the preparation of the mixture.

Comparative Example 3

A nanocrystal $CsPbBr_{1.92}I_{1.08}$ was obtained in the same manner as in Example 5, except that no tetradecylphosphonic acid was added during the preparation of a mixture.

Evaluation Example 1

1) Examples 1-5, Comparative Example 1, and Comparative Example 3

Photoluminescence spectra of the nanocrystals prepared according to Examples 1-5, Comparative Example 1 and Comparative Example 3 were analyzed. During analysis of the photoluminescence spectra, photoluminescence spectra immediately after preparation and photoluminescence spectra at 1 week at about 15 to about 25° C., a relative humidity of about 40 to about 70%, and 1 atm after preparation were examined, and the analysis results are given in FIGS. 3A to 3E, respectively. FIGS. 3A to 3E show photoluminescence spectra of the nanocrystals prepared according to Examples 1-4 and Comparative Example 3. In FIGS. 3A to 3E, As-synthesized represents nanocrystals immediately after preparation and Aged represents nanocrystals at 1 week after preparation.

The difference in maximum emission wavelengths of each nanocrystal was calculated according to the following Equation 1, and given in the following Table 1. The differences of maximum emission wavelengths were compared to examine degradation effects of individual nanocrystals. The maximum emission wavelength represents an emission wavelength showing the maximum intensity.

Emission wavelength difference (nm)={maximum emission wavelength of nanocrystal immediately after preparation–maximum emission wavelength of nanocrystal at 1 week after preparation}   Equation 1:

TABLE 1

| Section | Emission wavelength (nm) of quantum dot immediately after preparation | Emission wavelength (nm) of quantum dot at 1 week after preparation | Maximum emission wavelength difference (nm) |
|---|---|---|---|
| Example 1 | 700 | 700 | 0 |
| Example 2 | 650 | 649 | 1 |
| Example 3 | 680 | 640 | 40 |
| Example 4 | 680 | 642 | 38 |
| Example 5 | 640 | 635 | 5 |
| Comparative Example 1 | 700 | NA | NA |
| Comparative Example 3 | 610 | 550 | 60 |

In Table 1, NA represents not measurable.

Referring to Table 1 and FIGS. 3A to 3E, the photoluminescence spectrum of the quantum dot containing no phosphonic acid ligand of Comparative Example 3 immediately after preparation gave a red emission centered at about 610 nm. Here, the quantum dot does not contain phosphoric acid ligand. In contrast, its photoluminescence spectrum at 1 week after preparation gave an emission close to green centered at about 550 nm, suggesting that iodine with low stability is degraded within the quantum dot, and only the relatively stable bromide remains in the quantum dot, from which emission is observed in the aged sample. The quantum dot of Comparative Example 3 showed a photoluminescence wavelength shift, when comparing the quantum dot at 1 week after preparation with the quantum dot immediately after preparation, indicating that degradation of the quantum dot of Comparative Example 3 greatly occurred.

Unlike the quantum dot of Comparative Example 3, there was little change in the photoluminescence wavelength of the quantum dots prepared according to Examples 1, 2, and 5, when comparing the quantum dots at 1 week after preparation with the quantum dot immediately after preparation. The quantum dots prepared according to Examples 3 and 4 showed a small shift in the photoluminescence wavelength, compared to the quantum dot of Comparative Example 3. In other words, the quantum dots prepared according to Examples 1-5 showed a small peak shift even after 1 week, indicating their stability. Accordingly, it can be seen that the quantum dots of Examples 1-5 have improved stability, as compared to the quantum dot of Comparative Example 3.

Although the nanocrystal prepared according to Comparative Example 1 was stable immediately after synthesis, the quantum dot was damaged after several days, and thus impurities were notably observed. Since pure $CsPbI_3$ has very low stability, $CsPbI_3$ was degraded immediately after being synthesized, and therefore, it was difficult to photograph a stable spectrum.

2) Comparative Examples 1-3

Figure 2:
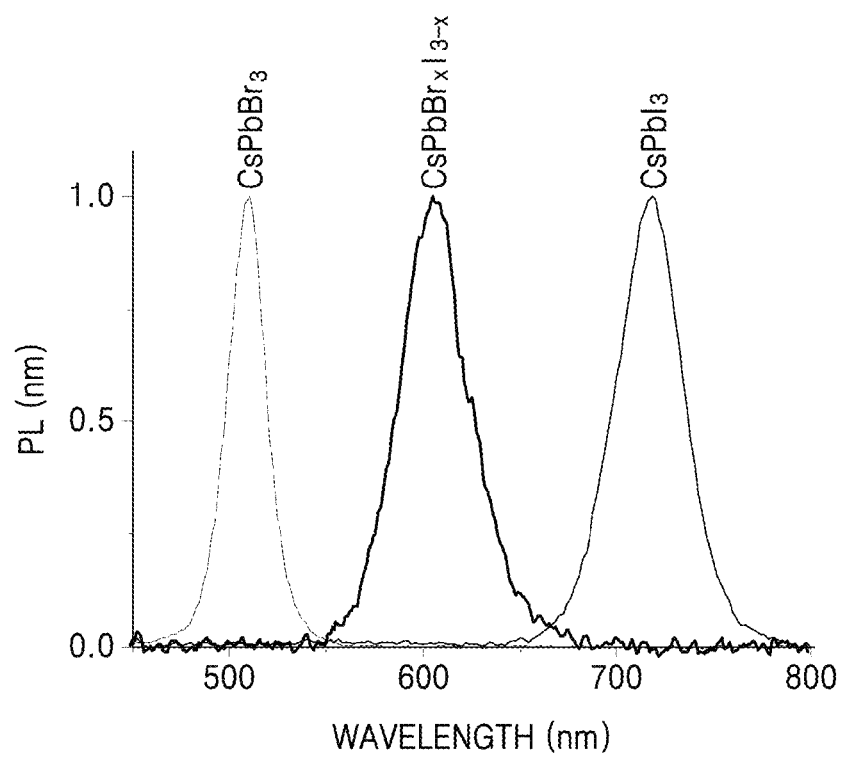
FIG. 2 shows photoluminescence spectra of quantum dots prepared according to Comparative Examples 1-3.
Figure 3A:
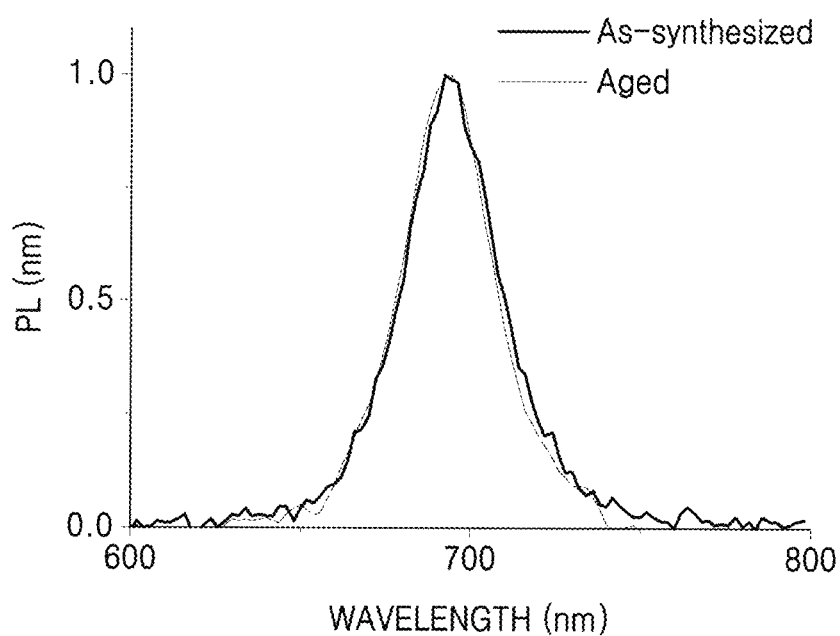
FIGS. 3A to 3E show photoluminescence spectra of quantum dots prepared according to Examples 1-4 and Comparative Example 3, respectively.
Figure 3B:
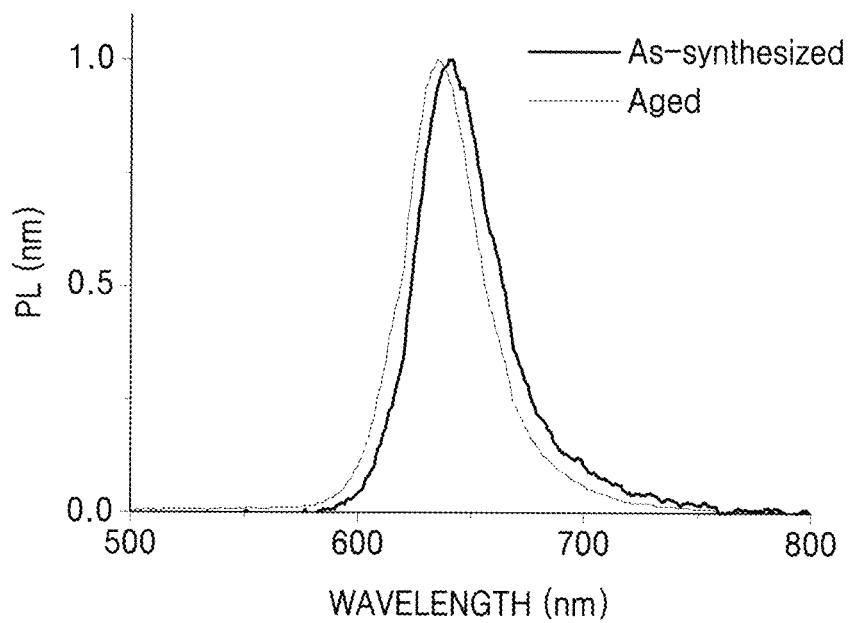
Figure 3C:
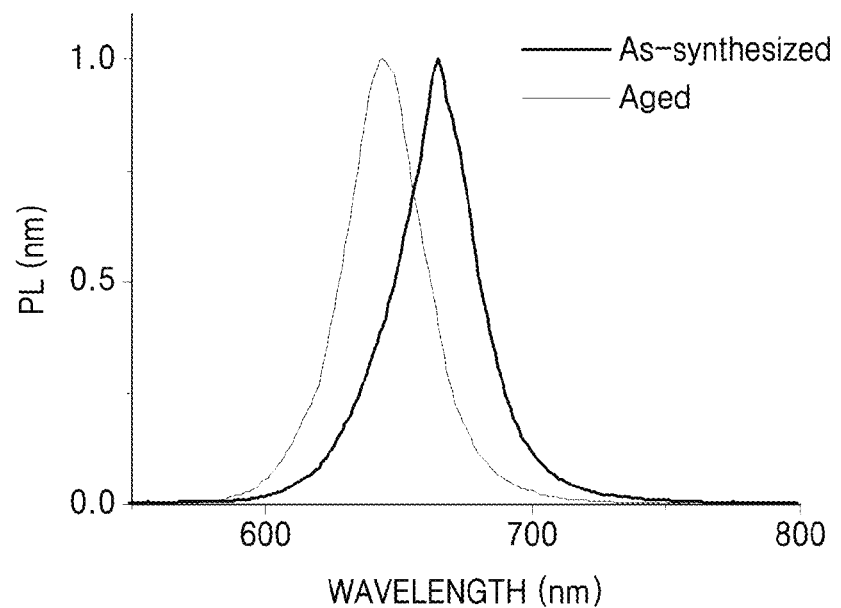
Figure 3D:
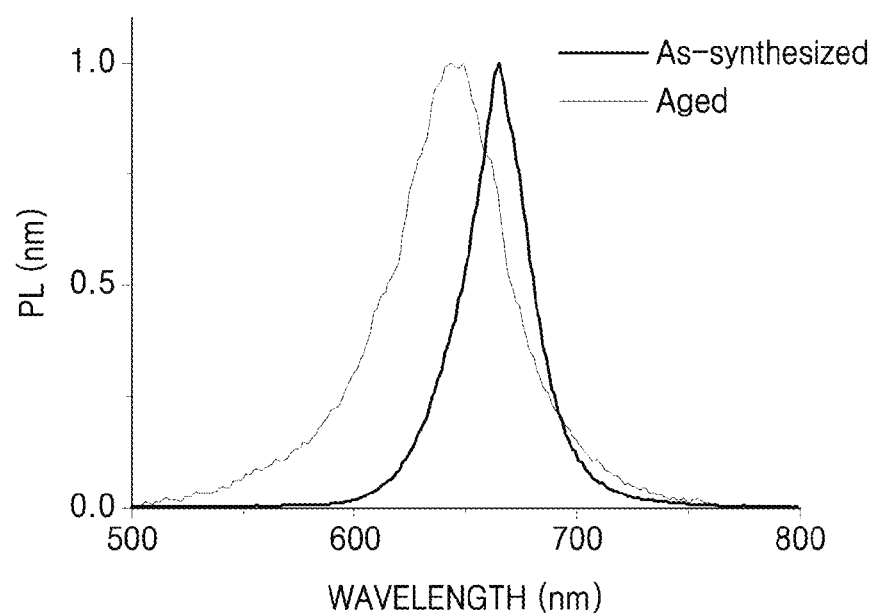
Figure 3E:
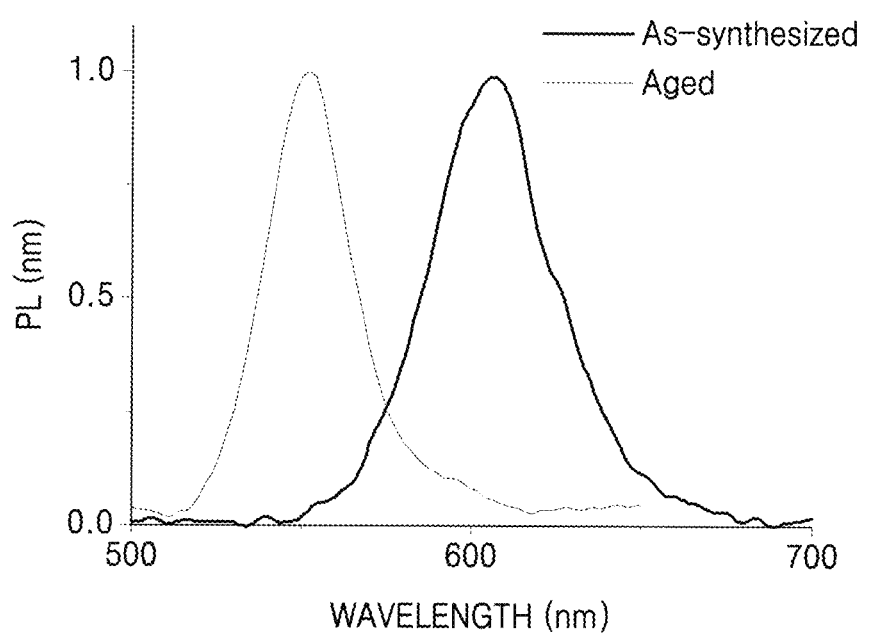

Photoluminescence spectra of the quantum dots prepared according to Comparative Examples 1-3 were analyzed and the results are given in FIG. 2.

Referring to FIG. 2, unlike general quantum dots with a size-tunable bandgap, perovskite quantum dots have a composition-tunable bandgap. For example, $CsPbX_3$ exhibits a green emission when X=Br, and a red emission when X=I, and thus various wavelength emissions may be obtained by a proper mixing thereof.

Evaluation Example 2: Ion Chromatography

Each 1 ml of nanocrystal solutions prepared according to Example 5 and Comparative Example 3 was mixed with 1 ml of water. While this mixture was left at about 25° C. over time, the amount of ions extracted from the nanocrystal to an aqueous layer was analyzed by ion chromatography. Herein, as the ion chromatography analyzer, Dionex ICS-5000+ HPIC ion chromatography, manufactured by Thermoscientific, San Jose, Calif., was used.

Figure 4A:
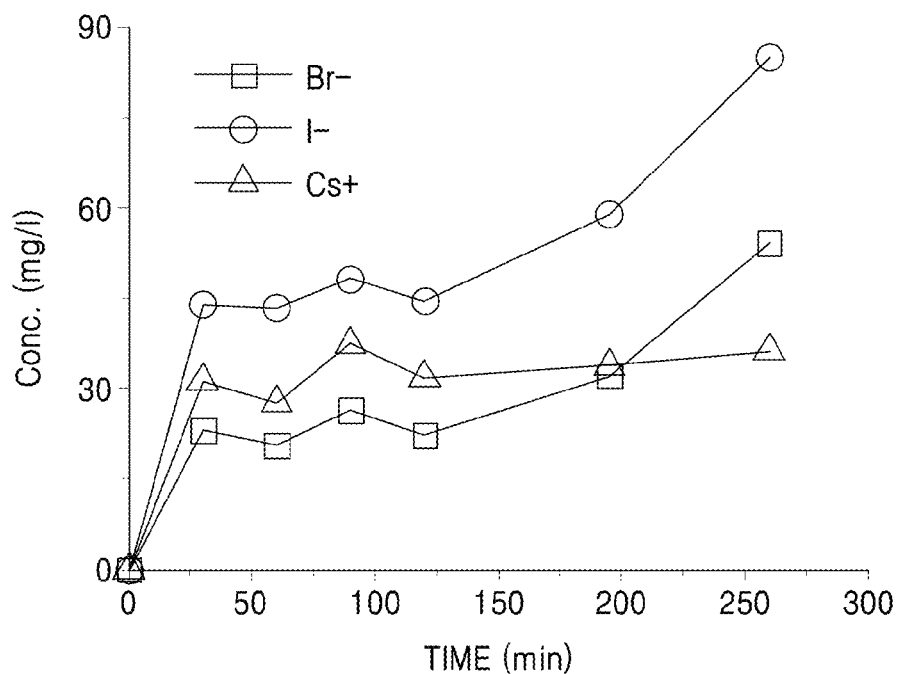
FIGS. 4A and 4B show results of ion chromatography analysis of quantum dot solutions prepared according to Example 5 and Comparative Example 3, respectively.
Figure 4B:
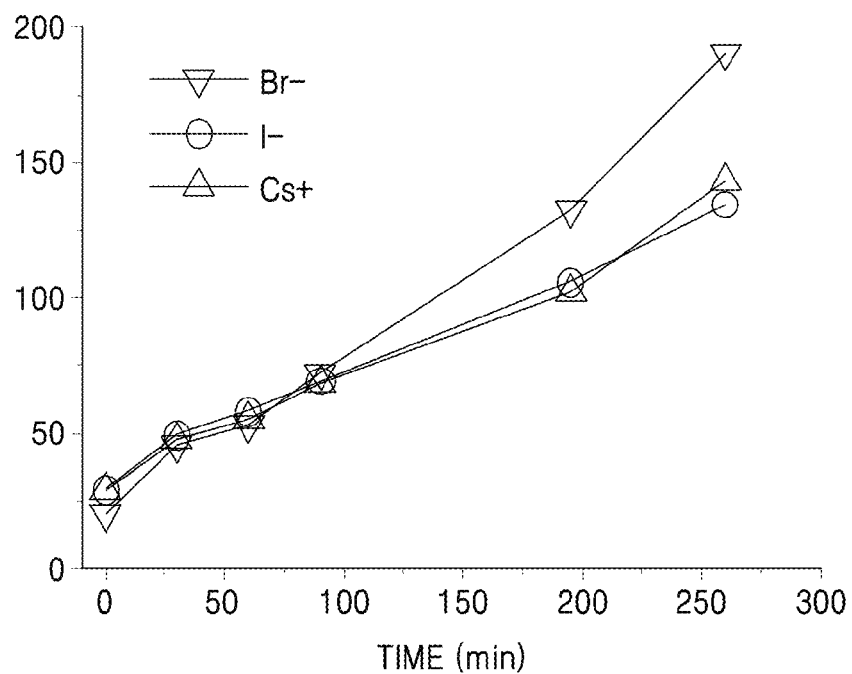
Figure 5A:
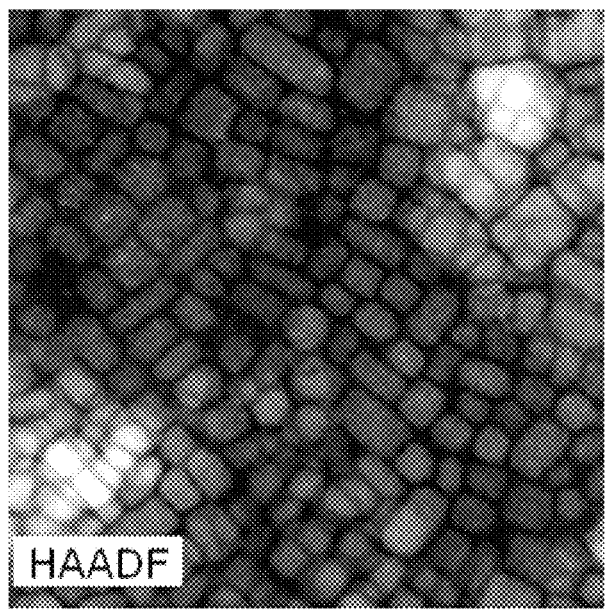
FIGS. 5A to 5F show results of energy dispersive spectrometer (EDAX) analysis of the quantum dot prepared according to Example 5.
Figure 5B:
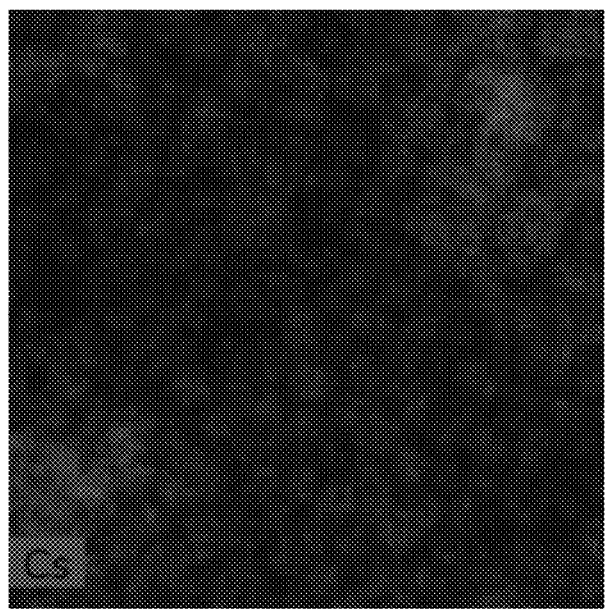
Figure 5C:
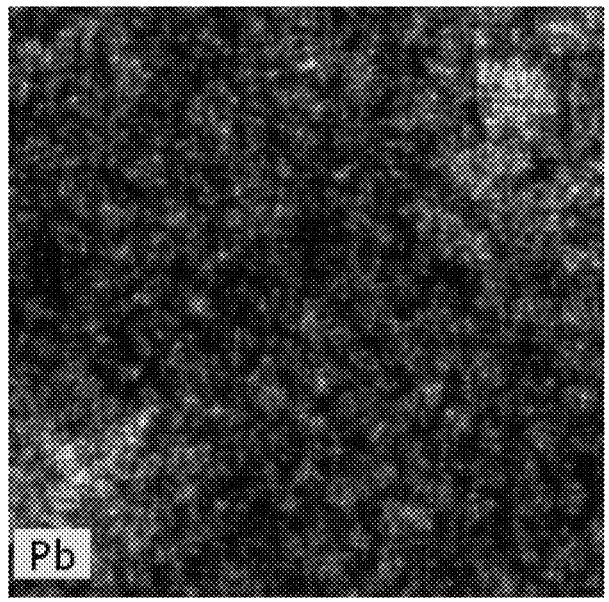
Figure 5D:
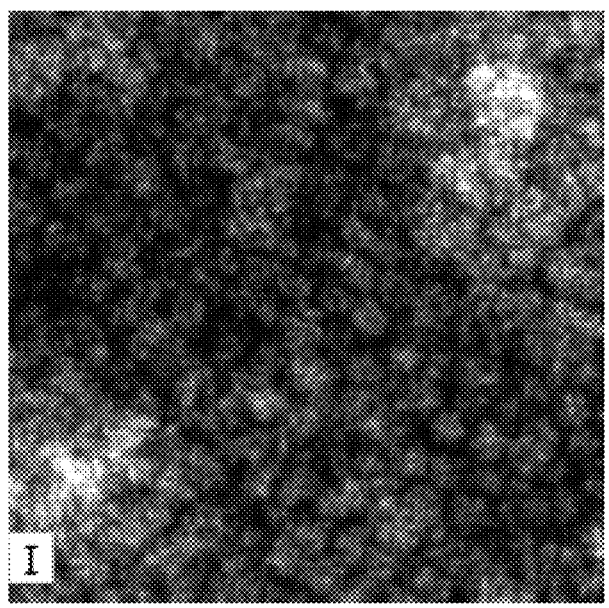
Figure 5E:
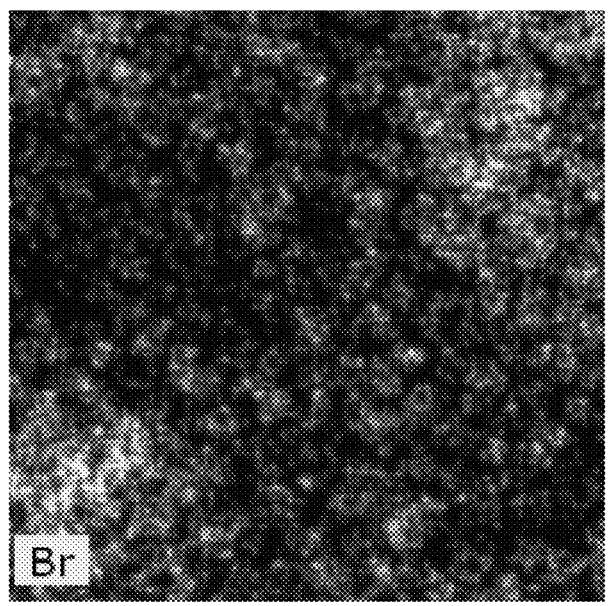
Figure 5F:
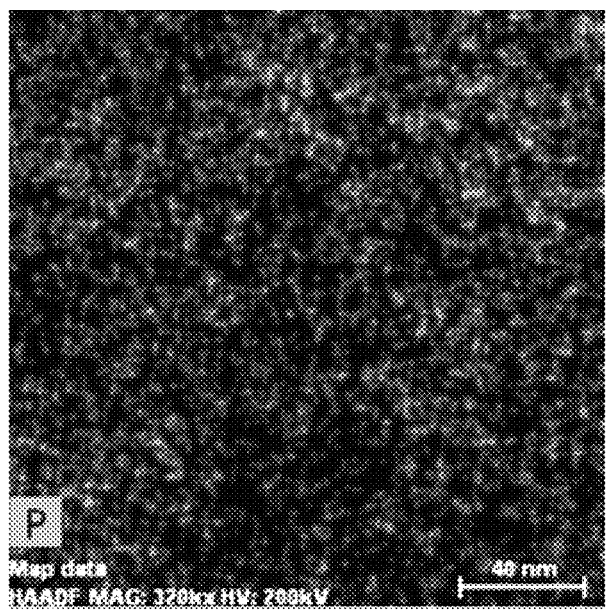

The results of ion chromatography analysis of nanocrystal solutions prepared according to Example 5 and Comparative Example 3 are given in FIGS. 4A and 4B, respectively. The content of bromine, iodine and cesium ions extracted from mixed solutions for about 4 hours are analyzed and given in Table 2.

TABLE 2

| Section | $Br^-$ (mg/l) | $I^-$ (mg/l) | $Cs^+$ (mg/l) |
|---|---|---|---|
| Example 5 | 48.1 | 77.3 | 35.5 |
| Comparative Example 3 | 173.2 | 126.3 | 131.7 |
| Content difference $(\Delta)^a$ (%) | 27.7 | 61.2 | 27.0 | a:(ion content of mixture of Example 5/ion content of mixture of Comparative Example 3)×100

Referring to Table 2 and FIGS. 4A and 4B, when the nanocrystal solution of Example 5 was used, the amount of extracted ions, in particular, iodine ion, was remarkably reduced. Therefore, it was confirmed that the stability of the nanocrystal of Example 5 was greatly improved as compared with the nanocrystal solutions prepared according to Comparative Example 3.

Evaluation Example 3: Energy Dispersive Analysis X-Ray (EDAX) Mapping

EDAX of the nanocrystal prepared according to Example 5 was performed, and the analysis results are given in FIGS. 5A to 5F.

Referring to these figures, it was confirmed that P coexists with Cs, Pb, I and Br in quantum dots.

Evaluation Example 4: Transmission Electron Microscopy

Figure 6:
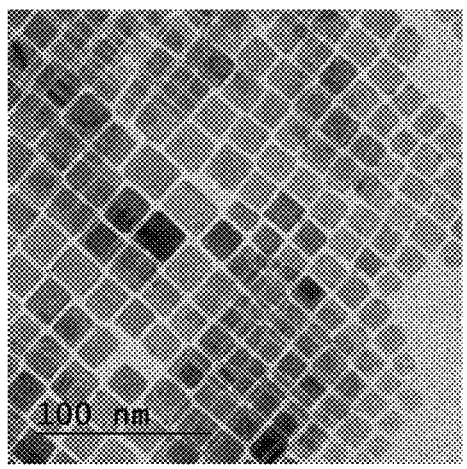
FIG. 6 shows results of transmission electron microscopy analysis of the quantum dot prepared according to Example 5.

The nanocrystal prepared according to Example 1 was analyzed by transmission electron microscopy, and the results are given in FIG. 6.

Referring to FIG. 6, it was confirmed that the nanocrystal has a cubic crystal structure.

It should be understood that embodiments described herein should be considered to be descriptive sense and do not limit the disclosure herein. Descriptions of features or aspects within each embodiment should typically be considered as being available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A nanocrystal represented by Formula 1:

$$AMX_3L \quad \text{Formula 1}$$

wherein A is selected from the group consisting of cesium (Cs), rubidium (Rb), and an ammonium salt, M is selected from the group consisting of germanium (Ge), tin (Sn), and lead (Pb), X is one or more selected from the group consisting of Cl, Br, and I, and L is $CH_3(CH_2)_6P(=O)(OH)_2$, $CH_3(CH_2)_7P(=O)(OH)_2$, $CH_3(CH_2)_8P(=O)(OH)_2$, $CH_3(CH_2)_9P(=O)(OH)_2$, $CH_3(CH_2)_{10}P(=O)(OH)_2$, $CH_3(CH_2)_{11}P(=O)(OH)_2$, or $CH_3(CH_2)_{12}P(=O)(OH)_2$.

2. The nanocrystal of claim 1, wherein the nanocrystal represented by Formula 1 is a compound represented by Formula 2:

$$AMI_xBr_{3-x}L \quad \text{Formula 2}$$

wherein A is selected from the group consisting of cesium (Cs), rubidium (Rb), and an ammonium salt, M is selected from the group consisting of Ge, Sn, and Pb, and $0<x\leq 3$.

3. The nanocrystal of claim 1, wherein the nanocrystal is a compound represented by the following Formula 3:

$$CsPbI_xBr_{3-x}L \quad \text{Formula 3}$$

wherein $0<x\leq 3$.

4. The nanocrystal of claim 1, wherein the nanocrystal is a compound represented by the following Formula 4:

$$CsPbI_xBr_{3-x}L \quad \text{Formula 4}$$

wherein $0<x\leq 3$.

5. The nanocrystal of claim 1, wherein $AMX_3$ in the nanocrystal is $CsPbI_3$, $CsPbBr_{1.92}I_{1.08}$, $CsPbBr_{1.8}I_{1.2}$, $CsPbBr_{1.7}I_{1.3}$, $CsPbBr_{1.6}I_{1.4}$, $CsPbBr_{1.1}I_{1.9}$, $CsPbBr_{1.2}I_{1.8}$, $CsPbBr_{0.9}I_{2.1}$, $CsPbBr_{0.7}I_{2.3}$, $CsPbBr_{0.5}I_{2.5}$, $CsPbBr_{0.3}I_{2.7}$, or $CsPbBr_{0.1}I_{2.9}$.

6. The nanocrystal of claim 4, wherein the nanocrystal represented by Formula 4 is a nanocrystal of $CsPbBr_{1.92}I_{1.08}$.

7. The nanocrystal of claim 1, wherein the nanocrystal is a colloidal perovskite quantum dot.

8. The nanocrystal of claim 1, wherein an emission wavelength of the nanocrystal is 500 to 700 nm, and a difference in the emission wavelength after 1 week is less than 50 nm.

9. The nanocrystal of claim 1, wherein a content of one or more selected from the group consisting of Cl, Br and I, when extracted from the nanocrystal to an aqueous layer, is 80 mg/l or less, and a content of one or more selected from the group consisting of cesium (Cs) and rubidium (Rb), when extracted from the nanocrystal to an aqueous layer, is 40 mg/l or less.

10. A method of preparing the nanocrystal of claim 1, the method comprising:

mixing a metal halide comprising one or more selected from the group consisting of germanium (Ge), tin (Sn), and lead (Pb) with a solvent to form a mixture, and drying the mixture to form a dried mixture; and adding, to the dried mixture, a surfactant, a compound comprising an organic functional group having one terminal as a phosphonic acid group, and an organic acid comprising one or more selected from the group consisting of cesium (Cs), rubidium (Rb), and an ammonium salt, followed by mixing and heat-treatment.

11. The method of claim 10, wherein the compound comprising an organic functional group having one terminal as a phosphonic acid group is added in an amount of 0.1 to 1 mole, based on 1 mole of the metal halide.

12. The method of claim 10, wherein the organic acid is at least one selected from the group consisting of cesium oleate and rubidium oleate.

13. The method of claim 10, wherein the heat treatment is performed at a temperature of from 100 to 200° C.

14. The method of claim 10, wherein the compound comprising an organic functional group having one terminal as a phosphonic acid group is 1-tetradecyl phosphonic acid, n-hexyl phosphonic acid, or n-octadecyl phosphonic acid.

15. The method of claim 10, wherein the metal halide is at least one selected from the group consisting of lead iodide ($PbI_2$), lead bromide ($PbBr_2$), germanium iodide ($GeI_2$), germanium bromide ($GeBr_2$), tin iodide ($SnI_2$), and tin bromide ($SnBr_2$).

16. The method of claim 10, wherein the surfactant is at least one selected from the group consisting of $C_1$-$C_{18}$ carboxylic acid, $C_3$-$C_{18}$ alkyl amine, and $C_1$-$C_{18}$ alcohol.

17. The method of claim 16, wherein the $C_1$-$C_{18}$ carboxylic acid is selected from the group consisting of oleic acid, octanoic acid, stearic acid, and decanoic acid, the $C_1$-$C_{18}$ alkylamine is selected from the group consisting of oleylamine, octylamine, hexadecylamine, octadecylamine, and tri-n-octylamine, and the $C_1$-$C_{18}$ alcohol is selected from the group consisting of oleyl alcohol, octanol, and butanol.

18. The method of claim 10, wherein the solvent is one or more selected from the group consisting of 1-octadecene, 1-decene, 1-undecene, 1-dodecene, 1-tetradecene, 1-hexadecene, and 1-eicosene.

19. The method of claim 10, wherein the drying is performed at a temperature of from 100 to 150° C.

* * * * *